(12) United States Patent
Spiegelberg (10) Patent No.: US 11,065,370 B2
(45) Date of Patent: Jul. 20, 2021

(54) DEVICE FOR DRAINAGE, IN PARTICULAR FOR THE DRAINAGE OF A CHRONIC SUBDURAL HEMATOMA

(71) Applicant: Primed Halberstadt Medizintechnik GmbH, Halberstadt (DE)

(72) Inventor: Andreas Spiegelberg, Horgen (CH)

(73) Assignee: Primed Halberstadt Medizintechnik GmbH, Halberstadt (DE)

( * ) Notice: Subject to any disclaimer, the term of this patent is extended or adjusted under 35 U.S.C. 154(b) by 491 days.

(21) Appl. No.: 15/579,017

(22) PCT Filed: Apr. 18, 2016

(86) PCT No.: PCT/DE2016/100183
§ 371 (c)(1),
(2) Date: Dec. 1, 2017

(87) PCT Pub. No.: WO2016/192705
PCT Pub. Date: Dec. 8, 2016

(65) Prior Publication Data
US 2018/0140754 A1    May 24, 2018

(30) Foreign Application Priority Data
Jun. 2, 2015   (DE) .......................... 102015108754.5

(51) Int. Cl.
*A61M 1/00*   (2006.01)

(52) U.S. Cl.
CPC ........ *A61M 1/0003* (2013.01); *A61M 1/0011* (2013.01); *A61M 1/0049* (2013.01); *A61M 2205/0272* (2013.01); *A61M 2205/106* (2013.01)

(58) Field of Classification Search
CPC .... A61M 2205/0272; A61M 2205/106; A61M 1/0015
See application file for complete search history.

(56) References Cited

U.S. PATENT DOCUMENTS 2,947,470 A * 8/1960 Heese ................. A61M 1/0023
604/134
3,115,138 A * 12/1963 McElvenny ......... A61M 1/0011
604/133

(Continued)

FOREIGN PATENT DOCUMENTS

DE        2945379 A1   5/1980
DE   11 2012 005513 T5   10/2014

(Continued)

*Primary Examiner* — Catherine L Anderson
*Assistant Examiner* — Arjuna P Chatrathi
(74) *Attorney, Agent, or Firm* — Norris McLaughlin, P.A.

(57) ABSTRACT

A device for drainage includes a tubular reservoir having a tubular pliable wall, a rigid cover, and a rigid bottom, and also includes at least one spring which applies a force that presses the cover and the bottom apart, wherein the cover is movable in the direction of the bottom in order to place the spring into a start position. One or more magnets are configured such that the magnets apply an additional force on the reservoir in such a way that a resulting force pressing the cover and the bottom apart is substantially constant across as the spring is deflected.

17 Claims, 5 Drawing Sheets

(56) References Cited

U.S. PATENT DOCUMENTS

| | | | | | |
|---|---|---|---|---|---|
| 3,779,243 | A | * | 12/1973 | Tussey | A61M 1/0011 604/133 |
| 3,939,830 | A | * | 2/1976 | da Costa | A61M 16/0009 128/205.18 |
| 3,991,763 | A | * | 11/1976 | Genese | A61M 27/00 604/133 |
| 4,278,089 | A | * | 7/1981 | Huck | A61M 1/0011 604/134 |
| 4,578,060 | A | * | 3/1986 | Huck | A61M 1/0011 604/133 |
| 4,957,487 | A | * | 9/1990 | Gerow | A61F 5/44 604/133 |
| 5,071,409 | A | * | 12/1991 | Rosenberg | A61M 5/486 604/119 |
| 5,628,305 | A | * | 5/1997 | Melker | A61M 16/0048 128/202.29 |
| 6,923,799 | B1 | * | 8/2005 | Asfora | A61M 1/0003 604/541 |
| 8,753,322 | B2 | * | 6/2014 | Hu | A61M 1/0066 604/319 |
| 2004/0064132 | A1 | * | 4/2004 | Boehringer | A61M 1/0031 604/543 |
| 2008/0312550 | A1 | | 12/2008 | Nishtala et al. | |
| 2014/0276339 | A1 | | 9/2014 | Wilson et al. | |
| 2014/0358096 | A1 | | 12/2014 | Song | |
| 2015/0013671 | A1 | * | 1/2015 | Costella | A61M 15/0086 128/200.23 |
| 2015/0300124 | A1 | * | 10/2015 | Mailand | E21B 34/102 166/332.8 |

FOREIGN PATENT DOCUMENTS

| | | |
|---|---|---|
| EP | 2 777 751 A2 | 9/2014 |
| WO | 2007/005851 A2 | 1/2007 |

* cited by examiner

Fig. 7

DEVICE FOR DRAINAGE, IN PARTICULAR FOR THE DRAINAGE OF A CHRONIC SUBDURAL HEMATOMA

BACKGROUND OF THE INVENTION

The invention relates to a device for drainage, in particular for the drainage of a chronic subdural hematoma (CSH).

Chronic subdural hematoma is a disease that is typically caused by a traumatic event in elderly patients. Bleeding occurs below the dura mater into the subdural space (space underneath). The bleeding usually comes to a halt under the pressure in the effusion (hematoma); however, secondary bleeding occurs to the extent to which the blood is broken down. It is therefore a chronic disease that can only be controlled by surgery. For this purpose, the skull is opened, the blood from the effusion is drained or, depending on the amount, cleared out or washed out. After this operation, postoperative bleeding and a recurrence of the condition are highly probable. Clinical studies have shown that the probability of recurrence will be significantly lower if a drainage catheter is inserted which drains off further blood for a few days. Such a drainage device is typically inserted on a gravity-induction basis by placing a collecting vessel (reservoir, drip chamber, bag) a few centimeters below the hematoma level so that the blood and possible wound fluid are discharged under low hydrostatically produced negative pressure.

The difficulty here is that the wound cavity is not completely filled with fluid, so that air can also be sucked in. It forms bubbles or foam and the gravity-based drainage is stopped.

Attempts have been made to use genuine suction drains, in which suction is effected mechanically by spring-loaded bellows or similar units or by vacuum bottles. However, negative pressures which exceed −30 mmHg damage the brain and are not allowed. Vacuum vessels with such a low negative pressure only suck a small portion (less than 5%) of their volume before the vacuum is exhausted. Due to their construction, bellow systems produce a negative pressure which declines to zero over the work volume so that in this solution the complete volume can also not be utilized for drainage.

Furthermore, products are known in which two plates connected to each other by a tubular membrane are pressed apart by one or more helical springs so that a negative pressure is produced inside. Such products also produce a negative pressure which declines from its maximum value to zero if the product is designed such that the springs are fully relaxed in the end position. Attempts have been made to design a system with preloaded springs in which the negative pressure declines to a value that is not equal to zero but defined by the preload. However, the achievable preload is limited for reasons of construction and the change in negative pressure over the work range is still too high.

Another problem arises if a liquor leakage develops after surgery. This is a situation in which cerebrospinal fluid (liquor cerebrospinalis, in short: liquor) escapes. In uncontrolled suction drainage, even at low pressure, a greater quantity of liquor can be sucked, which can cause damage to the patient and lead to death.

SUMMARY OF THE INVENTION

The object of this invention is to provide a device for the drainage of a chronic subdural hematoma by using a reservoir which, by virtue of design, produces an almost constant negative pressure, in particular in the range below 30 mmHg.

A further object of this invention is, in particular, to provide a device such that the volume flow, i.e. the volume sucked out per time period, is limited.

This task is solved by a device described and explained hereinafter. The features of the invention described in the following can be combined with each other in any useful way.

According to the invention, the task is solved by the combination of a tubular reservoir with pliable wall and rigid cover and bottom with at least one spring positioned inside or outside the reservoir. The at least one spring is placed such that it can press bottom and cover apart or move them away from each other. The at least one spring is preferably preloaded such that it is deformed only over a part of its spring deflection, so that its force and thus the negative pressure generated by it change only slightly. Furthermore, in this invention at least one magnet or several magnets are provided which compensate(s) for the characteristic of the at least one spring in such a manner that said force is kept at an almost constant value.

In other words, the at least one spring is preloaded such according to one embodiment of the invention that the distance between the start position of the at least one spring and its end position defined by the length of the reservoir is only a part of the complete spring deflection of the at least one spring. The length of the reservoir is its maximum extension in the direction of the spring's movement. Moreover, one magnet or several magnets is/are provided in this invention and configured to apply apart from the spring force an additional force on the reservoir such that a resulting force pressing the cover and bottom apart is substantially constant or preferably constant over that part of the spring deflection. For this solution, a large number of suitable magnet arrangements is possible and particularly preferred embodiments are described below.

In this context, substantially constant means that the amount of the force over that part of the spring deflection deviates by preferably not more than 50%, preferably not more than 40%, preferably not more than 30%, preferably not more than 20%, preferably not more than 10%, preferably not more than 5%, preferably not more than 1% from the average amount of the force over that part of spring deflection.

In an alternative embodiment, substantially constant means that a negative pressure in the reservoir corresponds to the force and is, over that part of the spring deflection of the at least one spring between the start position and the end position of the at least one spring, in the range between 20 and 40 mmHg, preferably in a range between 25 and 35 mmHg, preferably in a range between 27 and 33 mmHg, preferably in a range between 28 and 32 mmHg, preferably in a range between 29 and 31 mmHg. In a further embodiment of this invention, the preferred pressure ranges also apply, with the upper limit always being 30 mmHg.

In a preferred embodiment of the invention, the tubular reservoir with pliable wall and rigid cover and bottom is placed in a casing with at least one inner spring.

Preferentially, the tubular reservoir is provided with one or more connections for one tube each, and each of the tubes can be put into flow connection with the reservoir through these connections.

These connections preferably penetrate a wall of the casing and are closely connected with it and with the reservoir or sealed in them by means of sealing agents.

According to an embodiment of the invention, the casing is furthermore equipped with at least one connection. If the connection is opened in the casing, the tubular reservoir can freely expand and contract. If the connection is closed, expansion and contraction are blocked because in an interior space of the casing, in particular between a wall of the casing and a wall or the cover of the tubular reservoir, a positive or negative pressure is generated which impedes the movement of the wall of the tubular reservoir.

In a preferred embodiment of the invention, a flow limitation is provided in the connection in the casing, e.g. in the form of a flow resistor such as a semi-permeable membrane, a nozzle or a perforated plate which restricts the outflow of ambient air from the space between the wall of the casing and the wall of the tubular reservoir.

In a particularly preferred embodiment of the invention, the bottom of the tubular reservoir is connected to a (particularly lower) wall of the casing in a form-fit, force-fit or substance-locking manner such that the cover of the reservoir positioned opposite the bottom in the direction of the at least one spring's movement moves relative to the casing when the tubular reservoir expands or contracts.

Furthermore, in one embodiment of the invention at least one magnet is installed in or on the cover. In addition to this, at least one magnet or a paramagnetic, preferentially a superparamagnetic or ferromagnetic, body is provided in the wall of the casing opposite the cover, and orientated such that it applies an increasing magnetic force when the cover comes closer to the opposite wall. This means that with the decreasing force of the at least one spring an increasing magnetic force is applied which completely or partially compensates the reduction of the spring force. Moreover, the components can also be arranged the other way round, i.e. a possible paramagnetic, superparamagnetic or ferromagnetic body can be provided on the cover and the at least one magnet is installed on that wall of the casing.

Preferably, the one or more magnets or paramagnetic, superparamagnetic or ferromagnetic body act together such that a resulting force pressing the bottom and cover apart is substantially constant, is preferentially constant (see also above).

For tensioning the device, the reservoir can be sucked empty by means of an injection syringe or a similar instrument. In a preferred embodiment of the invention, the device is tensioned by moving the movable cover manually against the spring force and possible magnetic force.

In particular in the case of an arrangement in which the reservoir is placed in a preferentially hermetically tight casing (e.g. with the flow resistor for the volume flow restriction described above), an opening is provided according to an embodiment of the invention, through which a rod or similar object is pressed against the movable plate with the rod being sealed against the casing by a seal in a cylindrical guide.

In a preferred embodiment of the invention, a disk is installed under the opening and sealed with a bellows or an elastic membrane against the casing. Preferably, the disk diameter is greater than the opening so that in a rest position it can butt against a circumferential edge of the opening on the inner wall of the casing. The opening is preferentially dimensioned such that the user can put his/her finger or a suitable object through the opening and press the disk away from the inner wall of the casing against the movable cover of the reservoir and thus tension the device.

In a further preferred embodiment of the invention, an elastic pump chamber is installed in or on the wall of the casing for tensioning and connected to the atmosphere via a non-return valve and to an interior space of the casing via another non-return valve. The non-return valves are orientated such that they enable a flow from the atmosphere into the elastic pump chamber and from the elastic pump chamber into the interior space of the casing and block a flow in the opposite direction. If the pump chamber is activated, air is pumped into the interior space of the casing and the reservoir is compressed (tensioned) due to the built-up pressure.

Moreover, in an embodiment of the invention the at least one spring has a plurality of coils and is arranged in such a manner at a periphery of the cover and the bottom that the reservoir is supported by the coils of the at least one spring.

Furthermore, in an embodiment of the invention the device is provided with at least one spreader element to prevent the pliable wall of the reservoir from collapsing, particularly when the cover is moved towards the bottom. A spreader element can be, for example, a ring connected to the wall of the reservoir.

Moreover, in an embodiment of the invention the at least one spreader element is a plate which is installed in an interior space of the reservoir and preferably extends transversely to the deflection direction of the at least one spring.

More aspects and embodiments of the invention which can also be expressed as claims are listed as points in the following. The reference numerals given in brackets refer to the figures.

And a further aspect of the invention according to Point 1 also refers to a device for drainage:

Point 1: A device for drainage with:
a tubular reservoir (100) comprising a pliable wall (1) as well as a rigid cover (3) and a rigid bottom (2), and
at least one spring (4) which applies a force that presses the cover (3) and the bottom (2) apart, wherein the cover (3) is movable towards the bottom (2) to bring the spring in a start position.

Point 2: The device according to Point 1, wherein the device comprises one magnet or several magnets (11, 12), which are configured to apply an additional force on the reservoir (100) such that a resulting force pressing the cover (3) and bottom (2) apart is substantially constant over this part of the spring deflection.

Point 3: The device according to Point 1 or 2, wherein the at least one spring (4) is preloaded to such an extent that the distance between the start position of the at least one spring (4) and its end position determined by the length of the reservoir (100) is only a part of the complete deflection of the at least one spring (4).

Point 4: The device according to one of the Points 1 to 3, wherein the tubular reservoir (100) comprises at least one connection (5, 6) for connecting a tube.

Point 5: The device according to Point 4, wherein the reservoir (100) is arranged in a casing (7) of the device, and the at least one connection (5, 6) penetrates the casing (7) and is closely connected to the casing (7) and the reservoir (100) or sealed into them by means of a sealing agent.

Point 6: The device according to Point 5, wherein the casing (7) comprises at least one connection (8), through which ambient air can be let in and out of an interior space (102) of the casing (7) between a wall (7a) of the casing (7) and a wall (3) of the reservoir (100).

Point 7: The device according to Point 6, wherein in the at least one connection (8) a flow resistor (9) is provided, which limits the volume flow of ambient air.

Point 8: The device according to Point 7, wherein the flow resistor (9) is formed by one of the following elements:
a nozzle,
an element consisting of a plurality of nozzles,
a porous element,
a membrane which comprises one passage opening or a plurality of passage openings,
a membrane made of a gas-permeable material or comprising a gas-permeable material,
a membrane made of silicone rubber or comprising silicone rubber.

Point 9: The device according to one of the previous points, wherein the bottom (2) of the reservoir (100) is firmly attached to a wall (7b) of the casing (7) and the cover (3) is movably arranged in the casing (7) such that it can be moved relative to the casing (7).

Point 10: The device according to point 9, wherein at least one magnet (11) is provided on the cover (3), and wherein on a wall (7a) of the casing (7) opposite the cover at least one further magnet (12) is provided, wherein the at least one magnet (11) and the at least one further magnet (12) are orientated to attract each other.

Point 11: The device according to point 9, wherein at least one magnet (11) is provided on the cover (3), and on a wall (7a) of the casing (7) opposite the cover at least one body of magnetic, in particular of paramagnetic, superparamagnetic or ferromagnetic, material is provided, wherein an attractive force acts between the at least one magnet (11) and the at least one body (12).

Point 12: The device according to point 9, wherein on the cover (3) at least one body (11) of magnetic, in particular paramagnetic, superparamagnetic or ferromagnetic, material is provided, and wherein at least one magnet (12) is provided on a wall (7a) of the casing (7) opposite the cover (3), wherein an attractive force acts between the at least one magnet (11) and the at least one body (12).

Point 13: The device according to one of the previous points, wherein the at least one spring (4) has a multitude of coils (40) and is arranged at a periphery of the cover (3) and the bottom (2) such that the reservoir (100) is supported by the coils (40) of the at least one spring (4).

Point 14: The device according to one of the previous points, wherein the device comprises at least one spreader element (13, 14) for supporting the reservoir (100).

Point 15: The device according to point 14, wherein the at least one spreader element (13, 14) is a ring connected to the wall (1) of the reservoir (100).

Point 16: The device according to point 14, wherein the at least one spreader element (13, 14) is a plate (25) provided in an interior space (103) of the reservoir (100).

Point 17: The device according to one of the previous points, wherein an opening (15) is provided in a wall (7a) of the casing (7) opposite the cover (3).

Point 18: The device according to point 17, wherein the device comprises a movable disk (16) which is arranged in an interior space (102) of the casing (7) and opposite the opening (15), wherein the disk (16) is connected to the casing (7) by a membrane (17) or a bellows (17) to seal the casing so that it can be pressed manually against the cover (3) to preload the at least one spring (4).

Point 19: The device according to one of the previous points, wherein an elastic pump chamber is provided in or on the wall of the casing and connected to the atmosphere through a non-return valve and to an interior space of the casing by a further non-return valve such that the non-return valves enable a flow from the atmosphere into the elastic pump chamber and from the pump chamber to the interior space of the casing and block the flow in the opposite direction.

BRIEF DESCRIPTION OF THE DRAWINGS

In the following, further features and advantages of the invention will be explained in the description of embodiments with reference to the Figures. They show.

DETAILED DESCRIPTION OF THE INVENTION

Figure 1:
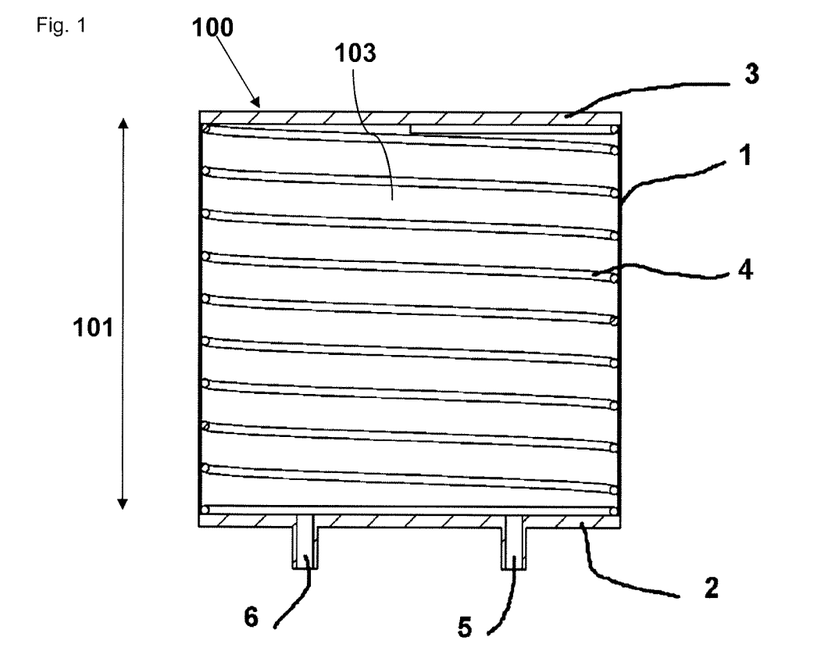
FIG. 1 a sectional view of an inventive device,
FIG. 2 a sectional view of the inventive device according to FIG. 1 with preloaded spring,
FIG. 3 a sectional view of a further inventive device,
FIG. 4 a sectional view of a further inventive device with several springs,
FIGS. 5-6 sectional detail views of an opening of an inventive device for preloading the spring(s) of the device,
FIG. 7 a graphic representation of the development of the negative pressure [mmHg] over the sucked-in volume [ml] of the device according to FIG. 3 with and without magnets.

FIG. 1 illustrates the functional principle of an inventive device. In the representation shown, the device comprises a reservoir 100, which has a rigid bottom 2 and a rigid cover 3 opposite the bottom 2. The bottom 2 and the cover 3 are connected to each other by a pliable, circumferential wall 1 so that said reservoir 100 is created.

In this embodiment, the pliable wall 1 of the reservoir 100 is, for example, a thin plastic film. The tube 1 is closed at its ends by the rigid bottom 2 and a rigid cover 3.

Furthermore, in an interior space 103 of the reservoir 100 a spring 4, preferably a helical spring 4, is installed which is preloaded against the bottom 2 and the cover 3 so that it tries to move the bottom 2 and the cover 3 apart. This means that the bottom 2 and the cover 3 of the reservoir 100 are positioned opposite to each other in the deflection direction of the spring 4 whereby the direction of movement is shown by 101.

The spring 4 is preloaded against the bottom 2 and the cover 3 such that in the fully expanded position (end position) shown in FIG. 1 it is already compressed preferably 50% to 70%, advantageously to 60%, of its expanded length. In the compressed position of the reservoir 100 or spring 4 shown in FIG. 2, the spring 4 is completely compressed in its start position. This means that its deflection is utilized by 50% to 70% or by 60% in particular.

Figure 2:
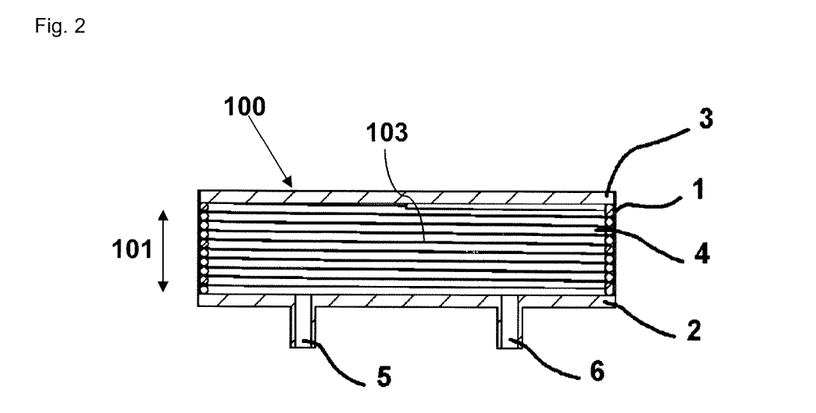

Moreover, the spring 4 is preferably designed such that in the completely compressed position (cp. FIG. 2) the then maximally possible spring force generates the negative pressure desired. In the completely expanded form shown in FIG. 1, the negative pressure ranges from 50% to 70% or is 60% of the value desired. So, the negative pressure does not change between zero and 100%, but it changes only between zero and 50% to 70% or zero and 60%. In this construction, the coils of the spring 4 continue to prevent the reservoir 100 from collapsing, in particular the pliable wall 1, when the reservoir 100 is being compressed.

Furthermore, the device or the reservoir 100 comprises a first connection 5 through which drained fluid can be sucked in the reservoir 100, and a second connection 6 through which said fluid can be discharged from the reservoir 100.

Figure 3:
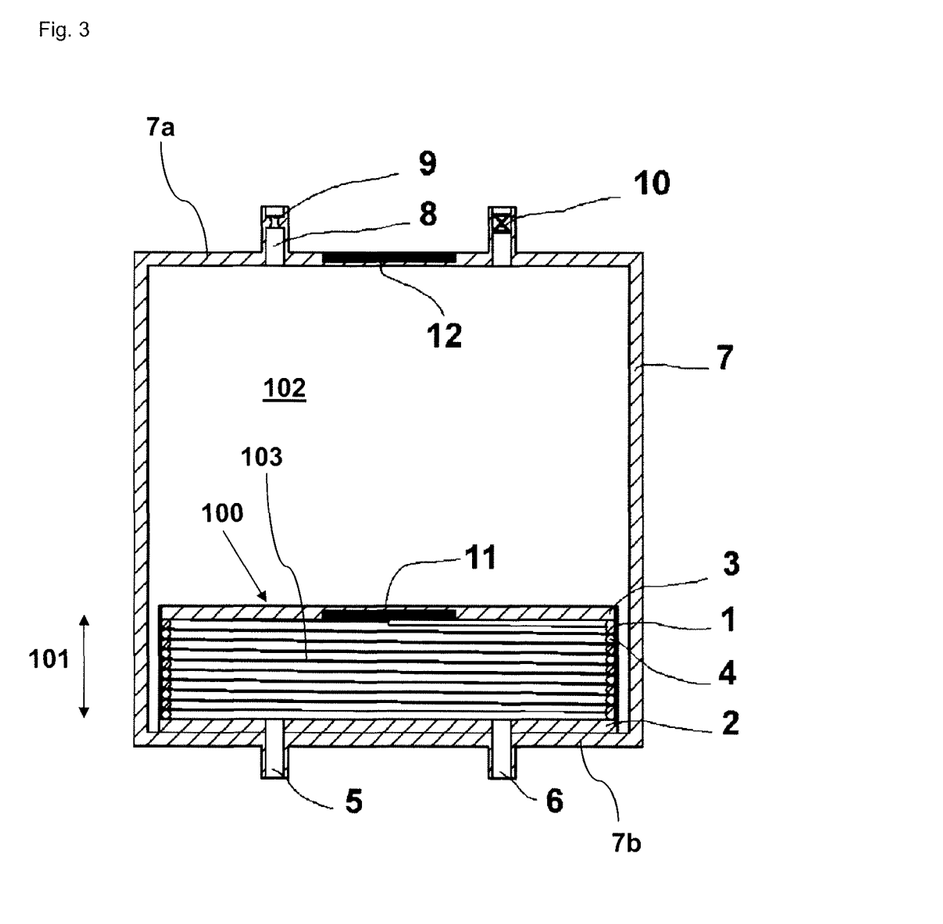

FIG. 3 illustrates a further embodiment of an inventive device, in which the reservoir 100 shown in FIGS. 1 and 2 is placed in a casing 7.

In this embodiment, the two connections 5 and 6 penetrate the casing 7.

The bottom 2 is connected to a wall 7b of the casing 7, whereas the cover 3 is movably arranged in an interior space 102 of the casing 100.

Moreover, the casing 7 is equipped with a connection 8 in which a flow resistor 9 is installed.

Moreover, a valve 10 is provided which, when being open, allows air flowing into the interior space 102 of the casing 7, i.e. between the casing 7 and a wall 1, 3 of the reservoir 100.

In addition, the device according to FIG. 3 preferably comprises a magnet 11 which is provided in the movable cover 3 of the reservoir 100, and a magnet 12 which is firmly arranged in the wall 7a of the casing 7 opposite the cover 3.

When the spring 4 expands, i.e. its force decreases, the magnet 11 approaches the magnet 12 and applies an increasing force on it which compensates the reduction of the spring force so that a resulting force which removes the cover 3 from the bottom 2 is as constant as possible (see above).

Figure 4:
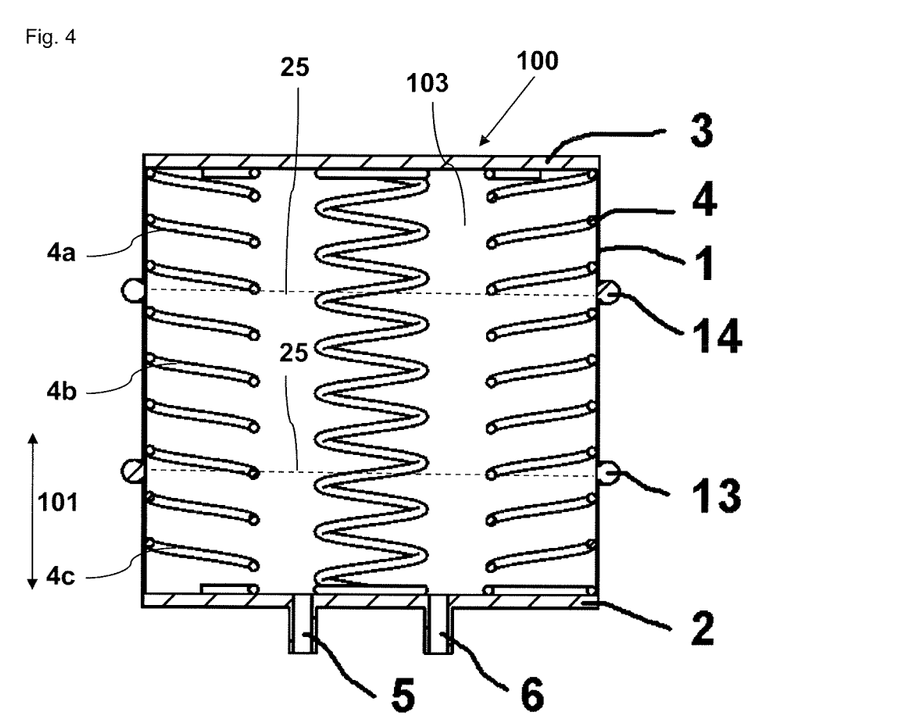

In the embodiment of the device or the reservoir 100 shown in FIG. 4, several springs are used which are arranged between the edges of the bottom 2 and the cover 3. In this embodiment, two spreader rings 13 and 14 are preferably installed on the circumferential wall 1 and prevent the tubular reservoir 100 from collapsing, e.g. similar to a bellows or a concertina. Instead of such spreader rings it is also possible to provide several plates 25 in the interior space 103 of the reservoir 100 which expand transversely to the springs 4 or the direction of movement 101 and rest on the wall 1. Such plates 25 can be penetrated by the springs 4. Each of the springs 4 can, however, also be divided accordingly, and then the resulting spring sections 4a, 4b and 4c rest at the then non-interrupted plates 25. The plates 25, for example provided instead of the spreader rings 13, 14, are shown in dotted lines in FIG. 4.

The configuration illustrated in FIG. 4 can of course also be arranged in a casing 7 which is for example designed as described above.

Figure 5:
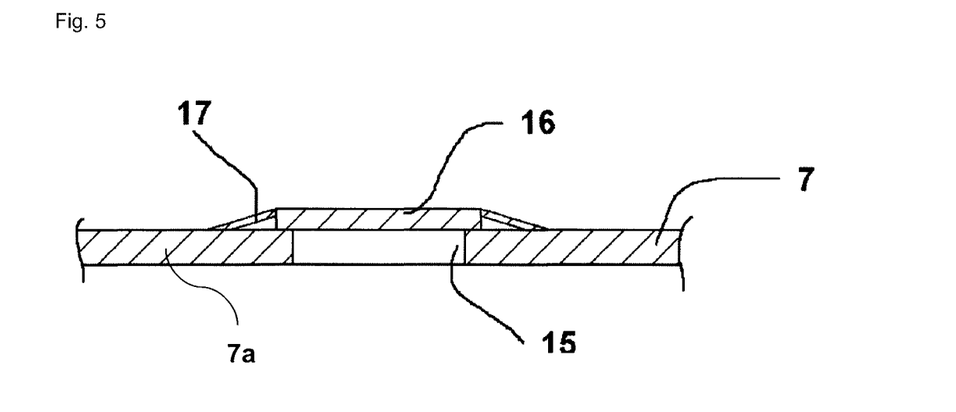
Figure 6:
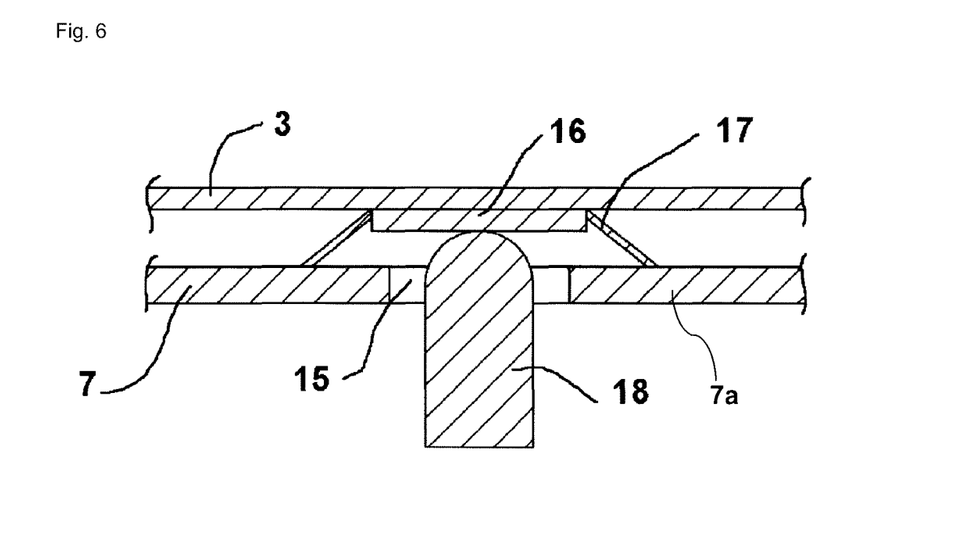

Moreover, FIG. 5 is a detailed illustration of a possible arrangement to preload the device which can be used for all embodiments comprising a casing 7. Here, an opening or borehole 15 is provided in the wall 7a of the casing 7 opposite the cover 3. A movable disk 16 is installed in the interior space 2 of the casing 7 and connected to the wall 7a of the casing 7 by an elastic membrane 17 or a bellows 17. If the user puts his/her finger 18 or a suitable object into the opening 15, as shown in FIG. 6, she or he can press the disk 16 against the cover 3 and thus preload the device or its spring(s) 4.

Figure 7:
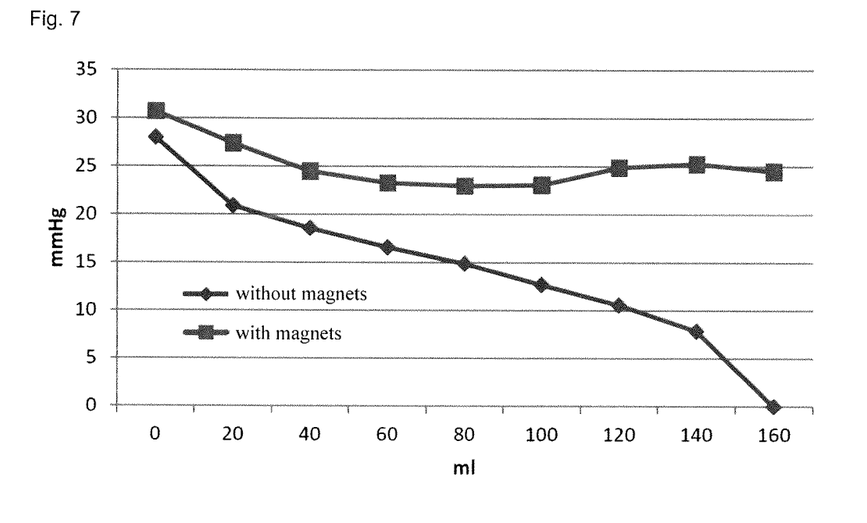

Finally, FIG. 7 shows the development of the negative pressure in the reservoir 100 as a function of the sucked-in volume of the device according to FIG. 3 with and without magnets 11, 12.

The invention claimed is:

1. A device for drainage comprising:
   a tubular reservoir comprising a tubular pliable wall and a rigid cover and a rigid bottom closing respective ends of the tubular pliable wall of uniform diameter and thereby constituting rigid walls of the reservoir, and
   at least one spring situated within the reservoir and configured to apply a force which urges the cover and the bottom apart, wherein the tubular reservoir is configured so that the cover is movable toward the bottom in order to compress the spring into a start position and at least one of the springs is configured to bear against the tubular pliable wall to retain the uniform diameter of the tubular pliable wall by preventing collapse of the tubular pliable wall when the reservoir is being compressed, and
   at least one magnet configured to apply an additional force on the reservoir in such a way that a resulting force pressing the cover and the bottom apart is substantially constant throughout deflection of the at least one spring from the start position to an end position defined by axial length of the reservoir,
   wherein the device for drainage is configured to produce a negative pressure not exceeding 30 mmHg.

2. The device according to claim 1, wherein at least one of the springs is preloaded such that the distance of deflection between the start position of the at least one of the springs is only a part of the maximum deflection of which the at least one of the springs is capable.

3. The device according to claim 1, further comprising at least one connection in the reservoir communicating with an interior space of the reservoir and configured for connecting a tube.

4. The device according to claim 3, further comprising a casing enclosing the tubular reservoir and the at least one spring, and wherein the at least one connection penetrates the casing and is closely connected to or sealed with the casing and the reservoir.

5. The device according to claim 4, further comprising at least one connection in the casing communicating with an interior space of the casing between at least one wall of the casing and at least one of the walls of the reservoir and configured to allow ambient air to flow into and out of the interior space of the casing.

6. The device according to claim 5, further comprising a flow resistor in at least one of the connections in the casing and configured to inhibit the flow of the ambient air.

7. The device according to claim 6, wherein the flow resistor is formed by an element selected from the group consisting of:
   a nozzle;
   an element consisting of a plurality of nozzles;
   a porous element;
   a membrane which comprises at least one passage opening;
   a membrane consisting of a gas-permeable material or comprising
   a gas-permeable material; and
   a membrane consisting of silicone rubber or comprising silicone rubber.

8. The device according to claim 4, wherein the bottom of the reservoir is fixed to a wall of the casing and the cover is movably arranged in the casing so that it can be moved relative to the casing.

9. The device according to claim 8, comprising a plurality of the magnets and wherein at least one first magnet is provided on the cover and at least one second magnet is provided on one of the walls of the casing which is opposite the cover, and wherein the at least one first magnet and the at least one second magnet are orientated such that they attract each other.

10. The device according to claim 8, wherein at least one of the magnets is arranged on the cover, and further comprising at least one body of magnetic, paramagnetic, superparamagnetic or ferromagnetic material on one of the walls of the casing which wall is opposite the cover, and wherein the at least one magnet and the body are so figured that an attractive force acts between the at least one magnet and the at least one body.

11. The device according to claim 8, further comprising at least one body of magnetic, paramagnetic, superparamagnetic or ferromagnetic material on the cover, and wherein at least one of the magnets is on one of the walls of the casing which wall is opposite the cover, wherein the at least one magnet and the body are so figured that an attractive force acts between the at least one magnet and the at least one body.

12. The device according to claim 1, wherein the at least one spring has a multitude of coils and is arranged at a periphery of the cover and the bottom in such a way that the reservoir is supported by the coils of the at least one spring.

13. The device according to claim 1, further comprising at least one spreader element configured to augment the at least one spring in bracing and thereby preventing collapse of the tubular wall of the reservoir.

14. The device according to claim 13, wherein at least one of the spreader elements comprises a ring connected to the tubular wall of the reservoir.

15. The device according to claim 13, wherein at least one of the spreader elements comprises a plate in an interior space of the reservoir.

16. The device according to claim 4, further comprising an opening in a wall of the casing opposite the cover.

17. The device according to claim 16, further comprising a button which is arranged in an interior space of the casing and opposite the opening in the casing, the opening being configured to provide manual access to the button, wherein the button is movably connected to the casing by a membrane or a bellows so that it can be pressed manually against the cover to preload the at least one spring and thereafter be returned to a rest position by the membrane or bellows.

* * * * *